United States Patent [19]

Coeurveille et al.

[11] Patent Number: 5,443,790
[45] Date of Patent: Aug. 22, 1995

[54] DEVICE FOR AUTOMATICALLY ANALYZING SAMPLES

[75] Inventors: Michel Coeurveille, Martignas sur Jalle; Christiane Rafilipomanana, Pessac; Yves Barach, Merignac; Magali Millet, Salles, all of France

[73] Assignee: Societe Francaise de Recherches et d'Investissements (SFRI), Martignas sur Jalle

[21] Appl. No.: 917,327

[22] Filed: Jul. 23, 1992

[30] Foreign Application Priority Data

Jul. 26, 1991 [FR] France ................ 91 09833

[51] Int. Cl.⁶ ............... G01N 35/02; G01N 21/00
[52] U.S. Cl. ............................ 422/63; 422/65; 422/67
[58] Field of Search .............. 422/63, 64, 65, 67; 435/292

[56] References Cited

U.S. PATENT DOCUMENTS

| | | | |
|---|---|---|---|
| 3,192,968 | 7/1965 | Baruch et al. | 422/67 |
| 3,772,154 | 11/1973 | Joenberg et al. | 435/292 |
| 3,912,456 | 10/1975 | Young | 422/67 |
| 4,731,225 | 3/1988 | Wakatake et al. | 422/65 |
| 4,738,824 | 4/1988 | Takeuchi | 422/63 |
| 4,774,055 | 9/1988 | Wakatake et al. | 422/64 |
| 4,803,050 | 2/1989 | Mack | 422/67 |
| 4,919,887 | 4/1990 | Wakatake | 422/67 |
| 4,931,402 | 6/1990 | Abplanalp | 435/291 |
| 4,933,146 | 6/1990 | Meyer et al. | 422/63 |
| 4,939,095 | 7/1990 | Yokotani | 422/64 |
| 4,979,821 | 12/1990 | Schutt et al. | 356/246 |
| 5,038,852 | 8/1991 | Johnson et al. | 422/116 |
| 5,051,238 | 9/1991 | Umetsu et al. | 422/67 |
| 5,055,408 | 10/1991 | Higo et al. | 422/65 |
| 5,084,242 | 1/1992 | Sakuma et al. | 422/63 |
| 5,176,880 | 1/1993 | Iwasaki et al. | 422/65 |

FOREIGN PATENT DOCUMENTS

| | | |
|---|---|---|
| 351988 | 1/1990 | European Pat. Off. |
| 3346532 | 7/1984 | Germany |
| 3441179 | 5/1986 | Germany |
| 2190999 | 12/1987 | United Kingdom |
| 8705401 | 9/1987 | WIPO |

Primary Examiner—Robert J. Warden
Assistant Examiner—Hien Tran
Attorney, Agent, or Firm—Sandler, Greenblum & Bernstein

[57] ABSTRACT

Device for enabling at least one analysis to be performed automatically on various samples is provided with at least one head having at least one first subunit for sampling and distributing liquids, a working surface for holding samples to be analyzed, reagents and reaction supports or vessels, a mechanical system for moving the at least one head within a horizontal plane above the working surface, at least one washing bowl to wash the at least one first subunit, at least one reading system to measure results of an analysis, and elements for controlling, checking and coordinating various stages of analysis. The device is particularly suitable for performing immunological tests.

12 Claims, 5 Drawing Sheets

DEVICE FOR AUTOMATICALLY ANALYZING SAMPLES

FIELD OF THE INVENTION

The present invention concerns a device enabling at least one analysis to be conducted on various samples so as to determine the presence or the quantity of at least one substance contained in the samples. More specifically, the present invention makes it possible to carry out immunological tests on biological liquids, such as serum and plasma, or to carry out biochemical tests.

BACKGROUND OF THE INVENTION

In the field of immunology, tests are generally carried out with a microtitration plate containing 96 reaction supports or vessels divided into 12 columns of 8 vessels. It is well known that the various stages of an immunological test on a microtitration plate may be carried out either manually or by means of automatic devices, but currently known devices only render automatic one portion of the various stages. For example, there currently exist devices which automate handlings of liquids, such as serum and reagents, but these devices neither manage the incubation times nor ensure the washing of the vessels and the readings at the end of reactions. One of the drawbacks relating to the carrying out of tests manually or by means of these devices resides in the difference in incubation times between the various vessels thus bringing about errors concerning the results. Another drawback is the use of a single technician, either to carry out manual operations or to transfer the plates from one device to another, for example, transferring liquids from an automatic manipulator to an incubator, then to a plate washer, then again to an automatic liquid manipulator, then to an incubator and finally to a 96 vessel plate reader.

European Patent application No. 0 351 988 discloses a device which automates the various stages of immunological tests, but this device ensures management per plate of 96 vessels and not per vessel. The main drawback of this device is not being able to mix on the plate various immunological tests having different incubation times between the stages.

Lack of flexibility, speed and accuracy, as well as risk of errors occurring due to handlings, has led us to produce a fully automatic device conforming to the invention.

There is also a large number of automatic devices for carrying out the stages of an immunological test on reaction supports specific to the device and not on the generally used supports, such as the vessel of a microtitration plate. The disadvantage is having to use only the reaction supports specific to the device. Moreover, with these devices, the user can carry out only one type of analysis at the same time per sample and must manually transfer the samples contained in their tube to the reaction supports specific to the device.

More specifically, the purpose of the invention is to resolve these drawbacks.

To this effect, the invention concerns a device for automatically analyzing samples, wherein it comprises:
  at least one head (1) comprising at least one subunit (23 to 26) for sampling and distributing liquids;
  a working surface (2) on which the samples to be analyzed (7,8), the reagents and the reaction supports or vessels (53) are disposed;
  a mechanical system (55 to 70) to move the head (1) inside a horizontal plane above the working surface (2);
  at least one washing bowl (37) to wash the subunit for sampling and distributing liquids;
  at least one reading system (38 to 45b, 72) for assessing the result of the analysis, and
  means (3, 4, 34, 73 to 80) for controlling, checking and coordinating the various analysis stages.

This type of device makes it possible to identify the samples, the reagents, the reaction vessels, to accurately handle the liquids, distribute reagents, mix them together, add them to a sample at the same time or at different times, to wash the reaction vessels so as to carry out readings by optical absorption or by measuring light emission or by reading a malfunction or by analyzing images. Preferably, the device comprises data processing means to control the various stages of an analysis for each reaction support, manage the reagent volumes, manage preservation of the reagents, extrapolate the results from calibration curves or threshold values, communicate with an external computer and memorize and store the analysis records and the results. Advantageously, it also comprises means to control its good working order and allow preventive maintenance to be carried out.

BRIEF DESCRIPTION OF THE DRAWINGS

Other characteristics and advantages relating to the constitution and functioning of various elements and subunits of the device shall appear more readily of a reading of the following detailed description of one embodiment of said device, this description being given solely by way of example, with reference to the attached drawings in which.

DETAILED DESCRIPTION OF THE PREFERRED EMBODIMENTS

Figure 1:
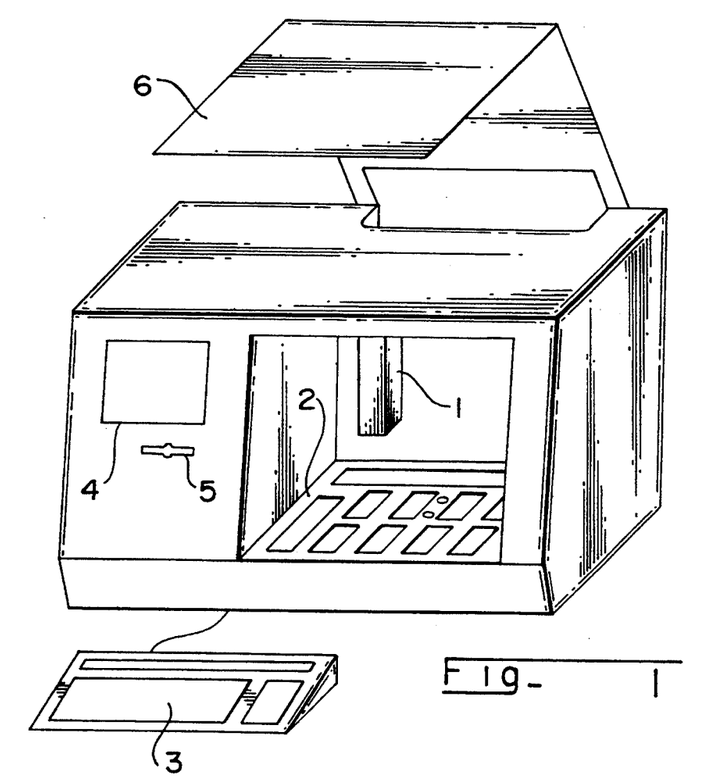
FIG. 1 shows a perspective view of an automatic device conforming to the invention.
Figure 2:
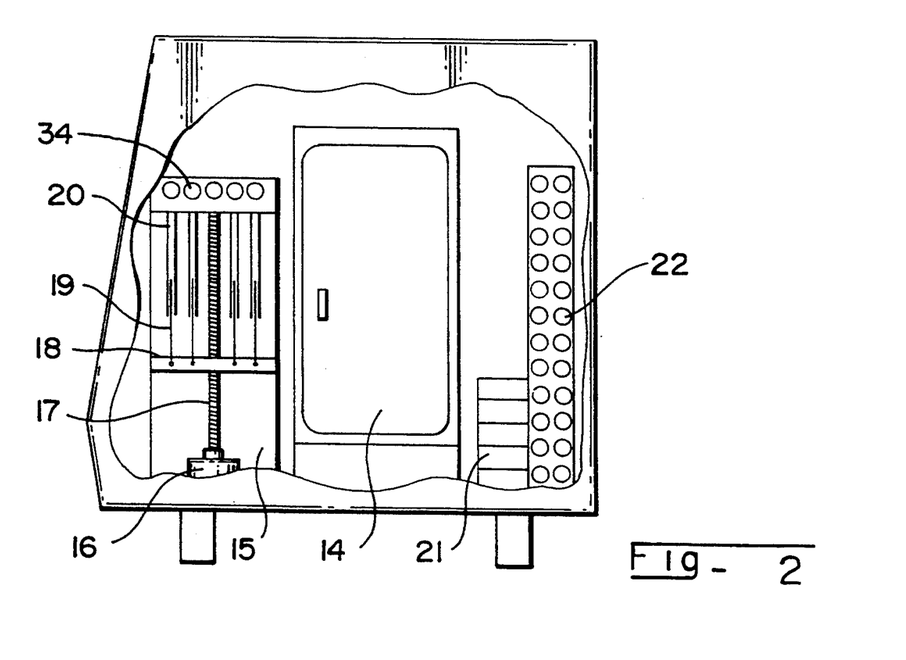
FIG. 2 is a front side view of the device of FIG. 1 with the inside of one portion of the device being shown.

FIGS. 1 and 2 feature the device for automatically analyzing samples so as to show the main elements. Certain subunits are shown in detail on FIGS. 3 to 11.

FIG. 1 shows the device with a single head (1). Other heads could be installed so as to increase the number of analyses.

FIG. 1 shows the head (1) which moves above the working surface (2). The keyboard (3) makes it possible to identify the samples and communicate with a first computer (see FIG. 11) which exchanges information with a second computer controlling the microprocessors which control motors or logical outputs-inputs. In the embodiment shown, the two computers are integrated in the device. The disk drive (5) is able to input programs, introduce protocols or receive results. The color monitor (4) is able to display information. When the system is working, the door (6) is shut and electromagnetically locked for safety reasons.

Figures 6, 7:
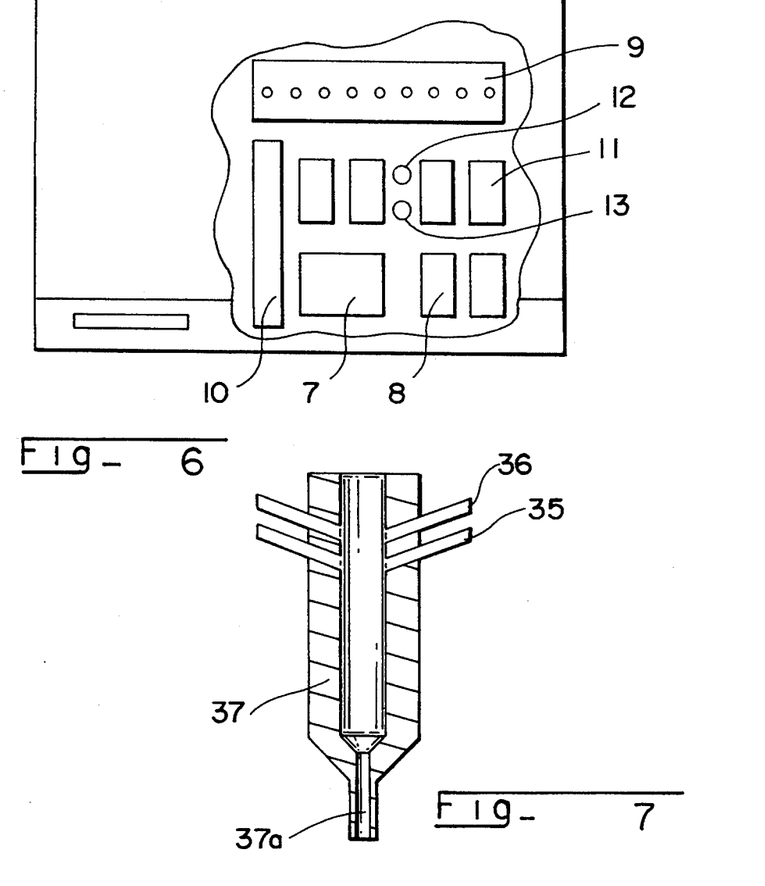
FIG. 6 is a plane top view of the device of FIG. 1 with one portion of the device being removed to show the working surface.
FIG. 7 is a partial cutaway view of the washing bowl.

On the working surface shown in FIG. 6, the samples to be analyzed are arranged at certain positions (7) or (8). The reagents specific to the analysis of a parameter are disposed in a zone (9) and the reagents common to several analyses, such as the solutions from dilutions of samples, are arranged in a zone (10) or in the box refrigerated via the Peltier effect shown at (14) on FIG. 2.

The conventional reaction supports or vessels are disposed on four plates, for example each plate having 96 reaction vessels. A plate is shown at (11). The zone (9) is refrigerated via the Peltier effect and can be shaken so as to homogenize the reagents.

Figure 3:
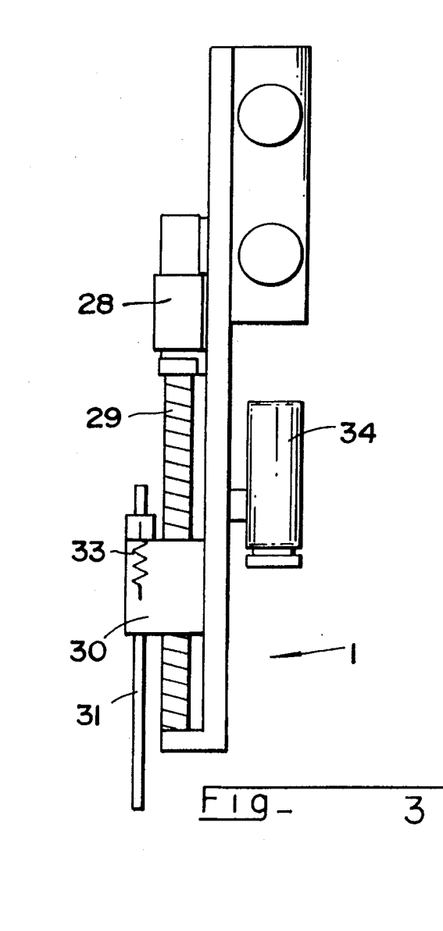
FIG. 3 is a side view of the head.
Figures 4, 5:
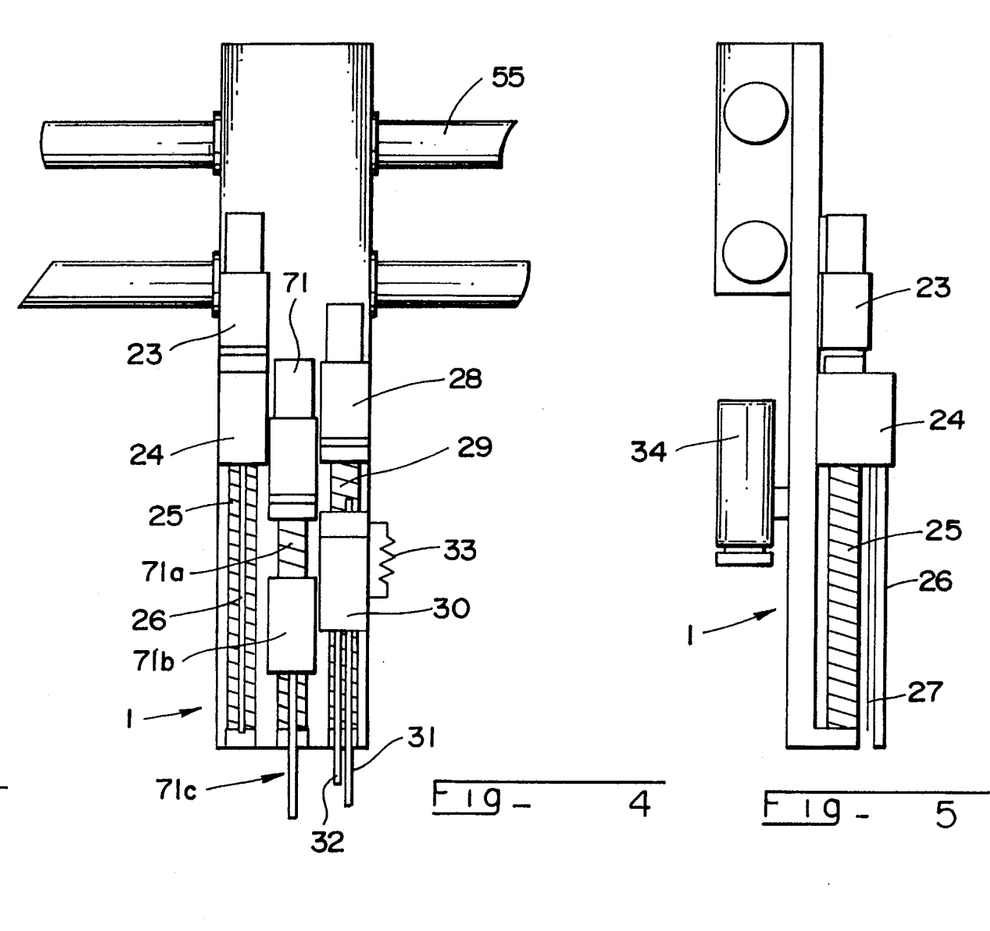
FIG. 4 is a lefthand view of the head and FIG. 5 is a righthand view.

The head (1) which moves above the working surface is shown in FIGS. 3, 4 and 5, and comprises three subunits, as shown in the embodiment. One of the subunits includes a motor (23) activating an endless screw (25) which moves a carriage (24). A pipette or small tube (26) is secured to the carriage, and in parallel, a conducting wire (27) is provided so as to detect the surface of the liquid to be sucked up. A second subunit includes a motor (28) which activates an endless screw (29) which moves a carriage (30). At least one subunit of two small tubes is secured to said carriage. One of the tubes (31) sucks up the liquid contained in a reaction support. This tube (31) is returned to the carriage by a spring (33). The carriage (30) lowers sufficiently so that the tube (31) touches the bottom of the reaction support and the spring when stretching keeps the tube firmly against the bottom whilst reducing the shock when the tube comes into contact with the bottom. The other tube (32) is used to send a washing solution into the vessels. Several subunits are provided so as to wash several reaction supports at the same time.

A CCD type camera (34) is also secured to the head. If the focus depth of the camera is sufficient, the latter may be integral with the head. This is shown in FIGS. 3 and 5. Otherwise, the camera may be integral with a carriage vertically moved by an endless screw, as the carriage (24) or (30) is moved.

The camera is able to analyze a label identifying a tube containing the sample or which identifies a box containing several reagents or which identifies a reaction support. The labels may be codified with bars. The camera can verify the position of the various elements on the working surface, namely sample tubes, reagents, reaction supports and thus control a possible error made by the operator when the working surface is loaded. Thus, the samples, reagents or reaction supports can be disposed on the working surface in appropriate positions but able to be differentiated by the operator, thus enabling the operator to eliminate any risks of errors occurring. Moreover, if, for example, the operator has forgotten to remove a stopper from a tube or flask containing a reagent, the latter shall be analyzed by the camera and the data processing system shall send a message to the operator and the analysis shall only start after the stopper has been removed. By image analysis, the camera may also interpret the result of a reaction and is able to measure an agglutination of immune complexes showing the presence of an "analyte" (antibody or antigen) in the sample. It is also able to locate the position of the head above the working surface. So as to adequately distribute or suck up the volume of samples and reagents between 1 $\mu l$ and 500 $\mu l$, the mechanical system is shown in FIG. 2. A motor (16) activates an endless screw (17) which makes the carriage (18) move vertically. The carriage is integral with four pistons (19) with syringes (20). One of the extremities of the syringes is integral with a mechanical frame (15). Pumps (21) may also be used to distribute volumes. A set of electrovalves (34) and (22) makes it possible to direct the liquids into the various pipes. Small tubes 26, 31 and 32 are connected to various electrovalves 22, 34 by pipes (not shown). When the small tube (26) has sucked up and then distributed with the aid of a mechanical system (15) a sample volume, it is then washed by being positioned inside a washing bowl (37) shown in FIG. 7 and at (12) on the working surface shown in FIG. 6. The head shall then move above the washing bowl, the motor (23) shall rotate the endless screw (25) and the latter shall lower the carriage (24) to which the small tube (26) and the wire (27) are secured. The small tube and the wire then enter the bowl (37). So as to wash the inside of the small tube (26), demineralized water, or a washing solution and then demineralized water shall arrive via the pipe connected at the top of the small tube (26), circulate inside the small tube and be ejected into the bowl (37) which is emptied through the orifice (37a) by means of a pump (not shown). So as to wash the outside of the small tube (26) and the wire (27), a washing solution and then demineralized water are injected by a number of nozzles (35), for example 6. To avoid the formation of droplets on the small tube or between the small tube (26) and the wire (27), air is injected through nozzles (36).

Figure 8:
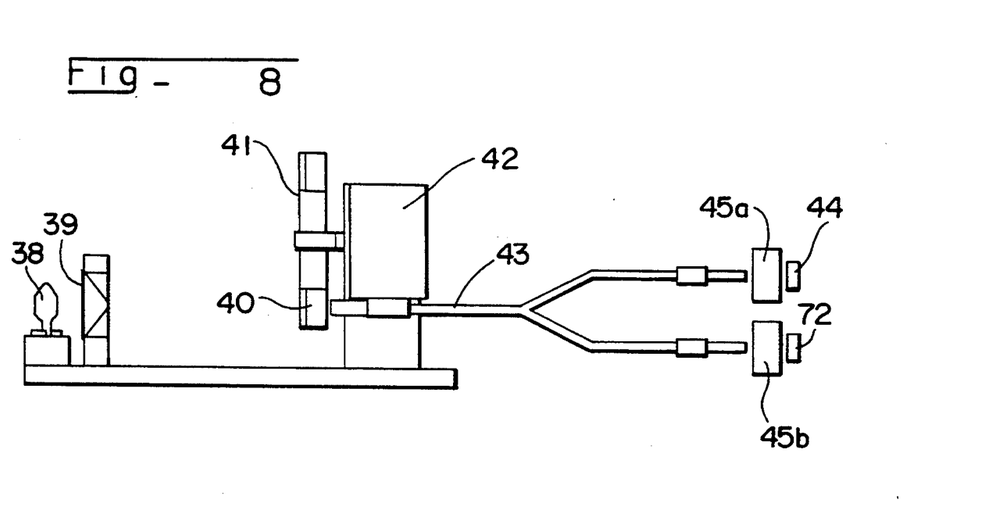
FIG. 8 is a diagramatical view of a reading system per measurement of the amount of light absorbed.

FIG. 8 shows a diagram of the reading system able to measure the amount of light absorbed by the reactional liquid. A lamp (38) emits light through a condenser (39) and a filter (40) secured to a turret head (41). The turret head (41) bearing ten different filters, is moved by the motor (42). After the filter (40), the optical light passes through a Y-shaped optical fiber (43) so as to send the light-towards two cells or photodiodes (44, 72) after having passed through two vessels or vats (45a, 45b), one (45a) containing the sample to be measured, the sample having been brought into the small tube (26) through the orifice (13) on the working surface.

Figure 9:
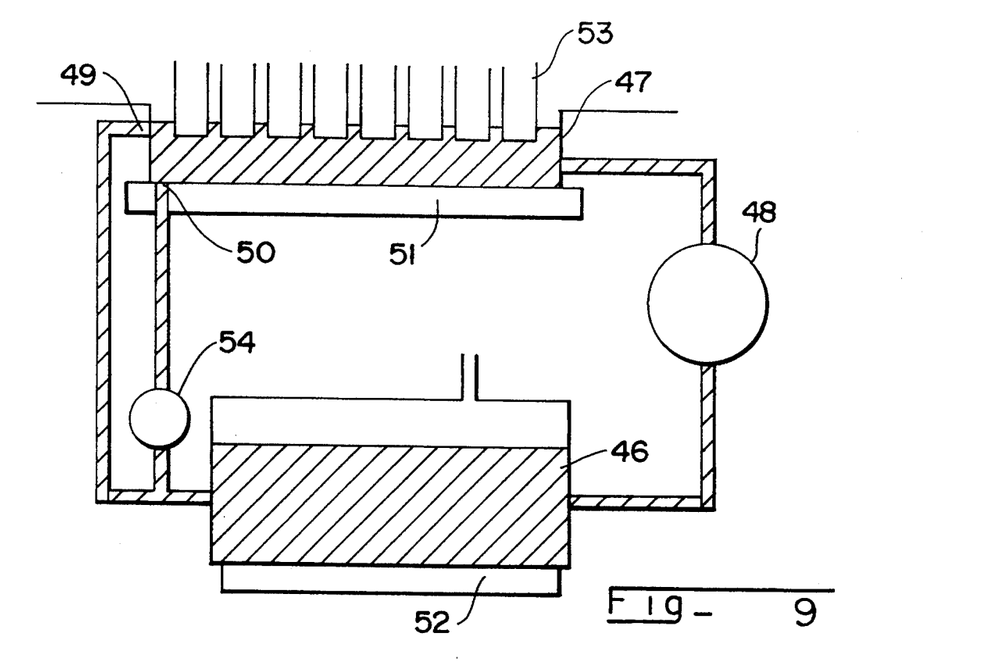
FIG. 9 is a cutaway diagramatical view of the thermic control system of the reaction vessels.

FIG. 9 shows a diagram of the thermic control system of the reaction supports (53). A tank (46) contains a liquid which circulates towards a vat (47) via a pump (48). The excess liquid in the vat is evacuated via an orifice (49). The liquid waters the bottom or one portion of the reaction supports according to the height of the orifice (49). A plate (51), whose temperature is regulated, makes it possible to heat the liquid whose temperature is also measured. A plate (52) is cooled via the Peltier effect and makes it possible to lower the temperature of the liquid. The Peltier effect may also be used to heat up the plate (52). Once the analyses have been completed, the vat (47) is emptied via the orifice (50) by activating the electrovalve (54).

Figure 10:
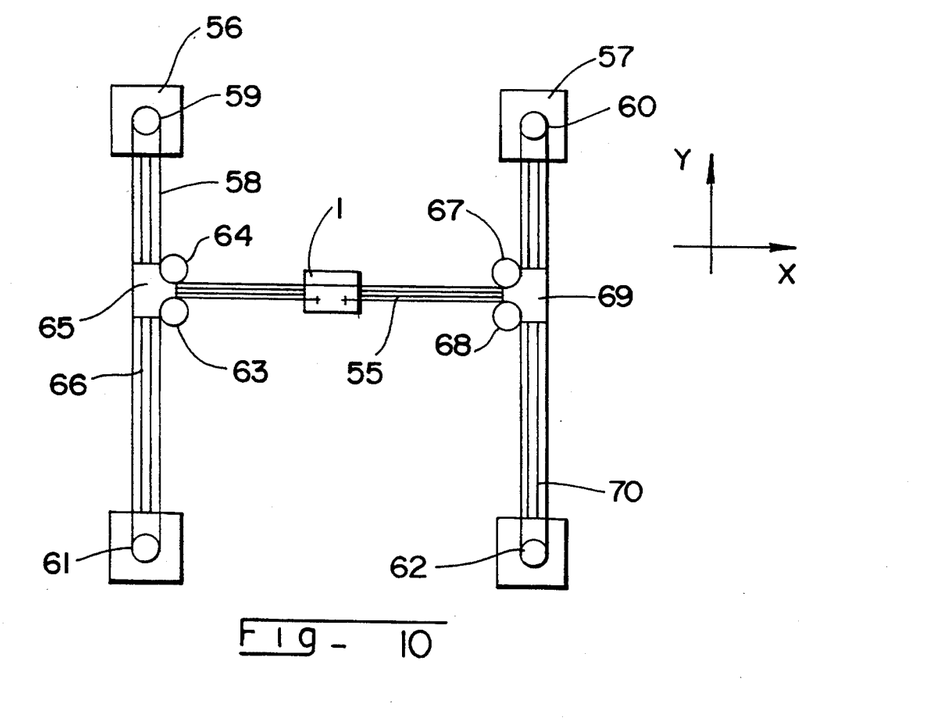
FIG. 10 is a diagramatical view of the mechanical system used to move the head.

The head (1) moves horizontally along the axes X and Y by means of a mechanical system shown in FIG. 10. Two motors (56) and (57) are fixed and with the aid of a set of pulleys drive a belt (58) integral with the head (1). Two pulleys (59) and (60) are integral with the axis of the motors. Pulleys (61) and (62) are fixed. Pulleys (63) and (64) are integral with a carriage (65) which moves on a bar (66). Pulleys (67) and (68) are integral with a carriage (69) which moves on a bar (70). The head (1) moves on bars (55). The two extremities of the belt (58) are secured to the head (1). The movement of the head is controlled via the direction of rotation of the motors and the number of revolutions effected by each motor.

Figure 11:
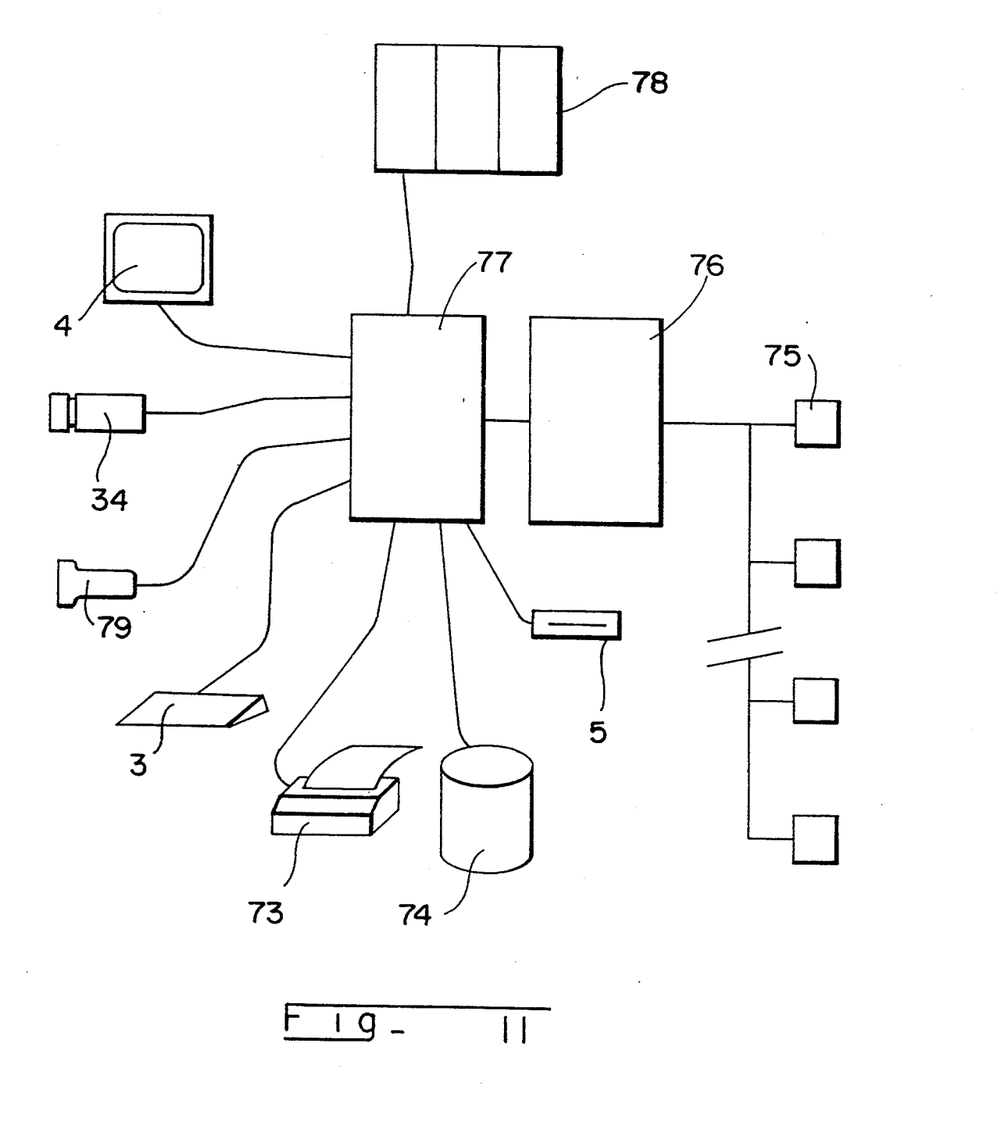
FIG. 11 shows a diagram of the data processing system.

Identification of the samples, reagents and reaction supports may be carried out either on the keyboard (3) or with the aid of a bar-code reader (79) or the CCD camera (34). The records of analyses are entered either on the keyboard (3) or input by a disk drive (5) so as to be stored on a hard disk (74). The results of analyses are edited on a printer (73), stored on the hard disk (74) and can be transmitted to an external central computer (78). The inputs and outputs described above are controlled by a computer (77). The computer (77) communicates with a computer (76) which controls microprocessors (75). These microprocessors manage the motors and logical inputs-outputs, such as the opening and closing of the door (6).

Both computers (76) and (77) may be located outside the automation. Only one computer may be used but the data processing system shall be less efficient.

With the aid of an example and with reference to the drawings, there now follows a description of one embodiment of the automatic device.

Identification of the serums to be analyzed is entered on the keyboard (3) as follows: the name of the patient, his number and desired analyses for one sample, for example, dosing of ferritin for the first sample.

The serum tubes with a diameter of 13 mm (74 mm high) are positioned in a rack arranged in a position (7) on the working surface. The tubes with a diameter of 9 mm (42 mm high) are positioned in one or two racks arranged in position (8).

After the serums have been identified, the data processing system, via one of the computers pools, analyses and shows how to position the reaction vessels and the plates with 96 positions and how to arrange the plates on the four positions (11). The system then ensures that the reagents belonging to each analysis have been properly positioned in zone (9), otherwise, it shall inform the user with the aid of the color monitor (4) of the location in zone (9) where a box of reagents needs to be added and asks the operator to identify the box with the aid of the keyboard (3) by indicating the name of the parameter and the batch number.

The system organizes the sequences of analyses with an appropriate software so as to optimize its movements and then it starts the analyses according to the records previously stored on the hard disk.

The motors (56) and (57) drive the belt (58) which moves the bar (55) along the axis Y and which moves the head (1) along the axis X. The head is positioned above the first sample tube, the motor (23) activates the endless screw (25) which moves towards the lower part of the carriage (24) integral with the small tube (26) and the wire (27) until the tube and wire meet the surface of the liquid sample. The motor (16) activates the endless screw (17) which moves the carriage (18) downwards driving the four syringes. One of the four syringes has a 500 $\mu l$ volume and the remaining three 2500 $\mu l$. By means of the set of electrovalves, the piston of the 500 $\mu l$ syringe whilst moving creates a partial vacuum in the small tube (26) so as to suck up a 20 $\mu l$ sample. The motor (23) makes it possible to lift up the carriage (24). The head is moved above the I reaction vessel (53) relating to the first analysis of the sample. The small tube (26) is lowered, the piston with the 500 $\mu l$ syringe is lifted up by the carriage (18) so that the 20 $\mu l$ sample are distributed inside the reaction vessel (53) whose walls are covered with anti-ferritin antibodies. Then, the head is positioned above the washing bowl shown in FIG. 7. The small tube (26) and the wire (27) are lowered. By means of the set of electrovalves, the pump (21) sends a washing solution and then demineralized water through the small tube (26), these solutions being evacuated from the washing bowl through the orifice 37a. At the same time, through six nozzles (35), washing solution jets and then demineralized water are sent onto the outside part of the tube. After a few seconds, preferably four, through two nozzles (36), an air jet prevents the formation of droplets on the tube. Finally, the carriage (24) lifts up, another cycle may be repeated so as to bring into the reaction vessel the 100 $\mu l$ of the reagent constituted for example by an antiferritin antibody conjugated with an enzyme, such as horseradish peroxidase.

The 20 $\mu l$ of serum is left to incubate for 30 minutes with the 100 $\mu l$ of the anti-ferritin antibodies conjugated with peroxidase in the presence of the additional anti-ferrin antibody secured to the walls of the vessel. During this time, the head may continue to transfer serums and conjugated antibodies into other vessels. After 30 minutes, under the control of the data processing system, the head takes position above the vessel (53).

The motor (28) activates the endless screw (29) so as to lower the carriage (33) until the tube (31) touches the bottom of the vessel and the contact is firmly maintained by the spring (33). Via the tube (31), by means of a pump (not shown), the liquid contained in the vessel is sucked up and then, via the tube (32) by means of another pump, a washing solution is distributed inside the vessel. This cycle may be repeated several times and these operations terminate by sucking up of the contents of the vessel. After the vessel is washed, the head moves slightly, a motor (71) by means of an endless screw (71a) moves a carriage (71b) bearing a set (71c) of small tubes. 100 $\mu l$ of a first reagent is distributed through one of the tubes and 100 $\mu l$ of a second reagent is distributed through the second tube. These two reagents are the substrate of the enzyme and are left to incubate for 15 minutes. During this time, the head may repeat the above-mentioned cycles concerning other vessels.

After 15 minutes, the liquid has taken on color in the vessel, the head is repositioned above the vessel and, with the aid of the small tube (26), 200 $\mu l$ of liquid are sucked up. The head moves above the reading vat (45a) situated under the orifice (13) and distributes 50 $\mu l$ which are immediately sucked up with the aid of a pump through the orifice situated at the bottom of the vat. This operation is intended to expel the residual matter from the previous sample which could falsify the reading by a change of color. The operation is repeated with a further 50 $\mu l$. Then, the remaining 500 $\mu l$ are distributed. The reading is carried out in the cell (44) through the 100 $\mu l$ of reactional liquid (vat 45a) and on the other cell (72) through a reference liquid (vat 45b). The 100 $\mu l$ reactional liquid is evacuated and replaced by the reference liquid and then the cells (44) and (72) are measured through the reference liquids. Thus, ageing of the vats is taken account of and in particular that (45a) which receives the reactional liquid. The result obtained is displayed on the screen (4), printed on the printer (73) and stored on the hard disk (74). If the automatic device is connected to a central computer (78), the latter can also stored the results for subsequent processing.

The device of the invention is more particularly intended for immulological tests in homogeneous or heterogeneous phases so as establish the dosage of an "analyte" known as a antibody or antigen, in a biological liquid. It is is also intended for determining the dosage of ADN—desoxyribonucleic acid—present in an extracellular position in the serum.

The example specified above does not restrict the invention to this embodiment. The invention also encompasses all other constructive variants.

Consequently, the subunits comprising the head (1) may be repeated eight times for one control by eight reaction supports at the same time instead of one. In this case, there shall also be both eight washing bowls (37) and reading systems.

What is claimed is:

1. Device for automatically analyzing samples, comprising:
    at least one head comprising at least one first subunit for sampling and distributing liquids, said first subunit comprising a first vertically movable carriage having at least one first tube for distributing and aspirating liquid product, said at least one first tube being connected to an aspirating and distributing system mounted on a frame;
    a working surface for fixedly holding samples to be analyzed, reagents and reaction supports;
    a mechanical system for moving said at least one head within a horizontal plane above said working surface, along two perpendicular directions, said mechanical system comprising a belt integral with said at least one head and driven by motors integral with said frame;
    at least one washing bowl positioned to wash said at least one first tube, said at least one washing bowl being constructed and arranged so that said at least one first tube is at least partially insertable therein, said at least one washing bowl comprising a lower orifice through which said at least one washing bowl is emptied, and said at least one washing bowl comprising at least one liquid injection nozzle for supplying washing solution to wash an outside portion of said at least one first tube when said at least one first tube is at least partially inserted in said at least one washing bowl;
    means for thermally regulating reaction the supports through a thermal regulating liquid in at least partial contact with said reaction supports;
    at least one reading system to measure results of reaction between samples to be analyzed and reagents; and
    means for controlling, checking and coordinating said at least one head, said mechanical system, said washing bowl, said means for thermally regulating said reaction supports and said at least one reading system to automatically analyze samples.

2. The device according to claim 1, wherein said at least one head comprises at least one second subunit for washing reaction supports.

3. The device according to claim 2, wherein said at least one second subunit comprises a second carriage secured to at least one second tube for aspirating liquid contained in the reaction support, and to at least one third tube for distributing a solution in the reaction support, said at least one second tube and said at least one third tube being connected to said aspirating and distributing system.

4. The device according to claim 3, including means for affixing said at least one second tube and said at least one third tube to said second carriage for ensuring sufficient contact with a bottom of the reaction support while compensating for possible height differences between bottoms of reaction supports.

5. The device according to claim 4, wherein said means for affixing comprise a spring.

6. The device according to claim 1, wherein said at least one washing bowl further comprises at least one injection nozzle for supplying air to dry the outside portion of said at least one first tube when said at least one first tube is partially inserted in said at least one washing bowl.

7. The device according to claim 1, wherein said at least one head comprises an additional subunit including a camera for analyzing at least one of (a) proper positioning of said at least one head, (b) identification codes associated with samples, and (c) results of an analysis.

8. The device according to claim 7, wherein said camera is fixed to said at least one head and said at least one head is vertically movable.

9. The device according to claim 1, wherein said at least one reading system comprises:
    a first vessel capable of containing a reference liquid;
    a second vessel capable of containing a sample;
    a Y-shaped optical fiber directing light towards each of said first vessel and said second vessel; and
    optical means for receiving light from said first vessel and said second vessel.

10. The device according to claim 9, wherein said optical means for receiving light comprise for each of said first vessel and second vessel a photodiode or a cell associated therewith and said second vessel.

11. The device according to claim 1, wherein said means for controlling, checking and coordinating comprise data processing means capable of storing records of analysis, control identification of samples and reagents and reactions supports, control analysis stages, and assist in operation and maintenance.

12. The device according to claim 1, wherein said means for thermally regulating comprise:
    a tank for containing the thermal regulating liquid;
    a vat for containing the reaction supports;
    a pump for circulating the thermal regulating liquid between said tank and said vat; and
    means for regulating temperature of the thermal regulating liquid.

* * * * *

UNITED STATES PATENT AND TRADEMARK OFFICE
CERTIFICATE OF CORRECTION

PATENT NO. : 5,443,790
DATED : August 22, 1995
INVENTOR(S) : M. COEURVEILLE et al.

It is certified that error appears in the above-indentified patent and that said Letters Patent is hereby corrected as shown below:

column 7, line 50 (claim 1, line 30), change "reaction the" to ---the reaction---.
    column 8, line 3 (claim 2, line 3), after "washing" insert ---the---.
    column 8, line 45 (claim 10, line 4), delete "and said second vessel".

Signed and Sealed this

Third Day of September, 1996

Attest:

BRUCE LEHMAN

*Attesting Officer*     *Commissioner of Patents and Trademarks*